United States Patent
Sano

(12) United States Patent (10) Patent No.: US 6,656,355 B2
(45) Date of Patent: Dec. 2, 2003

(54) APPARATUS FOR PREPARING DIALYSATE SOLUTIONS

(75) Inventor: Yoshihiko Sano, Osaka (JP)

(73) Assignee: Nipro Corporation, Osaka (JP)

( * ) Notice: Subject to any disclaimer, the term of this patent is extended or adjusted under 35 U.S.C. 154(b) by 75 days.

(21) Appl. No.: 09/903,715

(22) Filed: Jul. 13, 2001

(65) Prior Publication Data

US 2002/0011274 A1 Jan. 31, 2002

(30) Foreign Application Priority Data

Jul. 14, 2000 (JP) ........................... 2000-213968

(51) Int. Cl.⁷ ........................... B01D 61/26; B01D 61/28

(52) U.S. Cl. ........................... 210/321.71; 210/85; 210/86; 210/97; 210/194; 210/195.1; 210/252; 210/254; 210/258

(58) Field of Search ........................... 210/85, 86, 97, 210/103, 104, 194, 195.1, 252, 254, 258, 321.71; 137/896

(56) References Cited

U.S. PATENT DOCUMENTS

| | | | | |
|---|---|---|---|---|
| 4,037,616 A | * | 7/1977 | Pinkerton | 210/321.71 |
| 4,935,125 A | * | 6/1990 | Era et al. | 210/321.71 |
| 6,274,034 B1 | * | 8/2001 | Nikaido et al. | 210/321.71 |
| 6,277,272 B1 | * | 8/2001 | Nikaido et al. | 210/321.71 |

* cited by examiner

*Primary Examiner*—John Kim
(74) *Attorney, Agent, or Firm*—Kubovcik & Kubovcik

(57) ABSTRACT

A cost effective apparatus for preparing dialysate solution which can finely adjust the concentration of dialysate solution is described. The apparatus comprises a chamber 2, the inside of which is divided into three compartments 21, 22, 23 by a movable partitions 24, 25, a dissolving solution supply line 1 for supplying dissolving solution to the first compartment 21, a solution tank 5, a dialysate solution preparing line 31 connecting the solution tank 5 and the first compartment 21, a dialysate solution preparing line 32 connecting the solution tank 5 and the third compartment 23, a transporting pump 4 provided in the dialysate solution preparing line 32, a powder supply means 7 provided above the solution tank 5, and a dialysate solution transporting line 6 for transporting the dialysate solution prepared and filled in the third compartment 23 to the point of use, a by-pass line 81, and a circulating line 91.

9 Claims, 2 Drawing Sheets

APPARATUS FOR PREPARING DIALYSATE SOLUTIONS

TECHNICAL FIELD OF THE INVENTION

The present invention relates to an apparatus for preparing dialysate solutions wherein a powder including a granule is dissolved by a dissolving solution.

BACKGROUND OF THE INVENTION

Hitherto, preparation of dialysate solutions has been performed in a tank system. In the tank system, prescribed quantities of a dissolving solution and powder are introduced into a solution tank, and then stirred by a stirring pump or a stirring blade and mixed to form a dialysate solution. The prepared dialysate solution is transferred to a point of use by a delivery pump. At this time, the level of the solution in the solution tank is lowered, and a negative pressure is generated in the solution tank and thus outside air is introduced into the solution tank. The introduction of air occurs in the tank system because the solution tank is generally opened to the air to prevent breakage of the solution tank itself by a negative pressure generated therein. Therefore, in many cases, an air filter is provided at a portion opened to the air to prevent bacteria or the like contained in the outside air from entering. The use of an air filter results in problems and a high cost for replacing the air filter on a regular basis. As a matter of fact, there are cases where a filter that prevents only dust is used, or even no filter is used considering the above problems and cost, but this procedure is not preferable. In addition, in a tank system, when an attempt is made to prepare a large quantity of solution at a time, a large solution tank is necessary, thereby disadvantageously increasing the size of the apparatus itself. Moreover, since many stirring pumps and delivery pumps are necessary, the operating noise may disadvantageously be too loud. When an abnormal concentration is found after preparation, adjustment of the concentration of the dialysate solution cannot be made in the conventional tank system, whereby the dialysate solution has to be discarded. This is economically disadvantageous.

With a view to the circumstances described above, an object of the present invention is to provide a cost effective apparatus for preparing dialysate solutions in which replacement of an air filter for preventing bacteria or the like from entering into the solution tank is essentially unnecessary, and miniaturization of the entire system and lowering of operation noise are possible. Also, an object is to provide an apparatus for preparing dialysate solutions in which a concentration of a dialysate solution can be finely adjusted.

SUMMARY OF THE INVENTION

After dedicated studies, the inventor found that the above-described objects can be achieved by utilizing a chamber which is divided into three compartments, a first compartment, a second compartment and a third compartment, by movable partitions so that a dialysate solution can be prepared within a circuit containing the first compartment and the third compartment of the chamber while substantially preventing outside air from entering therein, and that the capacities of the first and the third compartments can be changed by changing the capacity of the second compartment, and reached the present invention. Stated differently, the present invention is an apparatus for preparing a dialysate solution comprising a chamber which is divided into three compartments, i.e., a first compartment, a second compartment and a third compartment, by movable partitions; a dissolving solution supply line for supplying a dissolving solution to the first compartment of the chamber; a dialysate solution preparing line connecting the first compartment and the third compartment of the chamber; a solution tank connected to the first compartment and a transporting pump connected to the third compartment and which are provided in the dialysate solution preparing line; powder supply means provided above the solution tank; a dialysate solution transporting line for transporting the dialysate solution prepared and filled in the third compartment to the point of use; a circulating line connecting the dialysate solution transporting line with the dialysate solution preparing line between the solution tank and the transporting pump, and a by-pass line for bypassing the solution tank and connecting the first compartment with the third compartment, in which the quantity of dissolving solution to be supplied to the first compartment and the quantity of dialysate solution to be transported to the third compartment can be adjusted by charging and a liquid to or discharging a liquid from the second compartment of the chamber.

The solution tank may be provided with a liquid level detecting sensor. It is preferable that a concentration meter is provided in the circuit comprising the third compartment of the chamber, the dialysate solution transporting line, the circulating line, and the dialysate solution preparing line. The dissolving solution supply line may be provided with a second dissolving solution supply line.

The apparatus for preparing a dialysate solution of the present invention is preferably constructed in such a manner that a second chamber which is divided into three compartments by movable partitions is connected to the dissolving solution supply line, the dialysate solution preparing line, and the dialysate solution transporting line so that the preparation of the dialysate solution can continuously be performed.

DETAILED DESCRIPTION OF THE INVENTION

Figure 1:
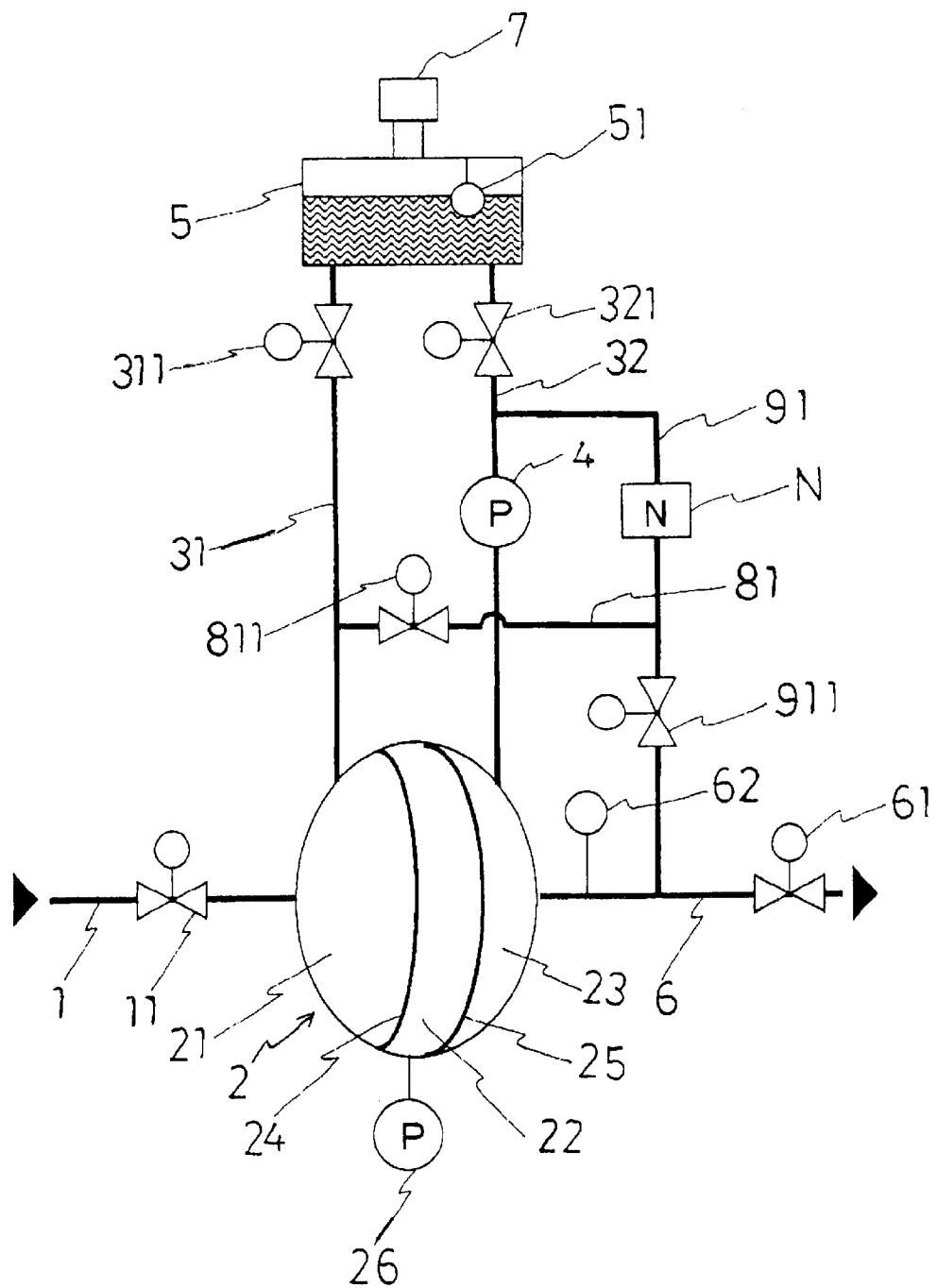
FIG. 1 is a schematic system diagram showing an embodiment of the present invention.

Referring now to the drawings, embodiments of the present invention will be described.

The apparatus for preparing a dialysate solution of the present invention comprises, as shown in FIG. 1, a chamber 2, the inside of which is divided into three compartments, a first compartment 21, a second compartment 22, and a third compartment 23, by movable partitions 24 and 25, a dissolving solution supply line 1 for supplying dissolving solution to the first compartment 21 of the chamber 2, a solution tank 5, a dialysate solution preparing line 31 connecting the solution tank 5 with the first compartment 21 of the chamber 2, a dialysate solution preparing line 32 connecting the solution tank 5 with the third compartment 23 of the chamber 2, a transporting pump 4 provided in the dialysate solution preparing line 32, a powder supply means 7 provided above the solution tank 5, a dialysate solution transporting line 6 for transporting dialysate solution prepared and filled in the third compartment 23 to the point of use, a by-pass line 81, and a circulating line 91, in which the quantity of the dissolving solution supplied to the first compartment 21 and the quantity of dialysate solution filled in the third compartment 23 can be adjusted by charging a liquid to or discharging a liquid from the second compartment 22 of the chamber 2.

The dissolving solution supply line 1, the dialysate solution preparing lines 31 and 32, the dialysate solution transporting line 6, by-pass line 81, and the circulating line 91 are provided with switch valves 11, 311, 321, 61, 811, and 911, respectively. The solution tank 5 is preferably provided with a liquid level detecting sensor 51, and the circuit comprising the third compartment 23 of the chamber 2, the dialysate solution transporting line 6, the circulating line 91, and the dialysate solution preparing line 32 is preferably provided with a concentration meter N for detecting an abnormality in concentration. The powder supply means 7 may be provided with an air filter (not shown) for preventing contamination caused by the incoming outside air.

The second compartment 22 of the chamber 2 is filled with a liquid such as silicone oil or the like such as to be charged and discharged by the pump 26.

The circulating line 91 is formed by connecting the dialysate solution transporting line 6 with the dialysate solution preparing line 32 between the solution tank 5 and the transporting pump 4 so that the solution in the third compartment 23 circulates from the third compartment 23 through the transporting line 6, the circulating line 91 and the dialysate solution preparing line 32 to the third compartment 23. The circulating line 91 comprises a line connecting an intermediate point of the dialysis solution transporting line 6 with an intermediate point located between the solution tank 5 and the transporting pump 4 in the dialysate solution preparing line 32. While circulating the solution, the valve 911 is opened but valves 61, 321 and 811 are closed.

The by-pass line 81 is formed by bypassing the solution tank 5 and connecting the first compartment 21 with the third compartment 23 so that the dissolving solution in the first compartment 21 is transported to the third compartment 23. The by-pass line 81 comprises a line connecting an intermediate point located between the first compartment 21 and the solution tank 5 in the dialysate solution preparing line 31 with an intermediate point located between the dialysate solution transporting line 6 and the dialysate preparing line 32 in the circulating line 91. That is, when transporting the dissolving solution by the transporting pump 4, the by-pass line 81 is connected to the line which is located downstream of the switch valve 911 and upstream of the transporting pump 4, and includes the circulating line 91 located downstream of the switch valve 911 and the dialysate solution preparing line 32 located upstream of the transporting pump 4, as shown in FIG. 1. While transporting the dissolving solution in the by-pass line 81, the valve 811 is opened but valves 321 and 911 are closed.

When performing a dialysate solution preparation operation, first, the switch valves 11, 311, and 61 are opened and the switch valves 321, 811 and 911 are closed, and then the dissolving solution is supplied from the dissolving solution source (not shown) through the dissolving solution supply line 1 to the first compartment 21 of the chamber 2 (step 1).

Then the movable partitions 24, 25 are pushed by the supplied dissolving solution and moved toward the third compartment 23, and the air contained in the third compartment 23 is discharged through the dialysate solution transporting line 6. The movement of the movable partitions 24, 25 continues until the capacity of the third compartment 23 becomes zero. In other words, it continues until the dissolving solution of the same quantity as the difference between the capacity of the chamber 2 and the capacity of the second compartment 22 is filled in the first compartment 21. As the supply of dissolving solution continues, the dissolving solution is then supplied to the solution tank 5 through the dissolving solution preparing line 31 (step 2).

When the level of the dissolving solution supplied to the solution tank 5 reaches a prescribed level that can be determined arbitrarily (step 3), the liquid level detecting sensor 51 is activated to close the switch valves 11, 61 but maintain the valve 311 open. The switch valve 321 is opened but switch valves 811 and 911 remain closed, and the transporting pump 4 is activated. The supply of a prescribed quantity of powder from the powder supply means 7 to the solution tank 5 is continuously performed from the beginning to the end of the operation of the transporting pump 4, for example (step 4).

When the transporting pump 4 is operated, a solution which is a mixture of powder and dissolving solution in the solution tank 5 is transported to the third compartment 23 through the solution preparing line 32, and simultaneously, the dissolving solution in the first compartment 21 of the same quantity as the dialysate solution transported to the third compartment 23 is supplied to the solution tank 5 through the dialysate solution preparing line 31. Since the valves 811 and 911 are closed, the dialysate solution cannot flow through the circulating line 91 or by-pass line 81. At this time, the movable partitions 24, 25 move toward the first compartment 21, and the movement of the movable partitions 24, 25 continues until the capacity of the first compartment 21 becomes zero, in other words, until the solution of the same quantity as the difference between the capacity of the chamber 2 and the capacity of the second compartment 22 is filled in the third compartment 23. During this process, the liquid level in the solution tank 5 is maintained at a constant level, and thus an influx of the outside air into the solution tank 5 hardly occurs (step 5).

The dialysate solution transporting line 6 between the third compartment 23 and the switch valve 61 is provided with a pressure gauge 62. When this pressure gauge 62 detects an increase in the internal pressure in the third compartment 23, that is, when the capacity of the first compartment 21 becomes zero and the internal pressure of the third compartment 23 increases (step 6), the switch valves 311, 321 are closed and the switch valve 911 is opened but the valve 61 remains closed. At this time, the solution transported to the third compartment 23 is circulated in the circuit connecting the dialysate solution transporting line 6, the circulating line 91, and the dialysate solution preparing line 32 by the transporting pump 4 (hereinafter referred to as circuit circulation of a solution) (step 7). The circuit circulation of a solution terminates at the moment when a prescribed time period has passed (for example, two or three minutes).

Ordinarily, preparation of the dialysate solution terminates when a normal (desired) value is detected by the concentration meter N on completion of the circuit circulation of the solution. But when a low concentration is detected by the concentration meter N on completion of the circuit circulation of the solution, it is necessary to supply powder to the solution tank 5 to increase the concentration of the solution in the solution tank 5, then to operate the pump 26 and open the switch valve 321 while discharging the silicone oil from the second compartment 22 by the pump 26, and to supply a quantity of solution of high concentration in the solution tank 5 corresponding to the quantity of the discharged silicone oil to the third compartment 23 (step 7-A). However, in this case, since the concentration adjustment is difficult and it has to be done again if the concentration becomes too high, the concentration of the solution for circuit circulation is practically set to a slightly higher value in advance so that concentration adjustment can be accomplished with one adjustment.

Alternatively, when a high concentration is detected by the concentration meter N upon completion of circuit circulation of the solution, the circuit circulation of the solution is started again (step 7), and simultaneously, the switch valve 11 is opened and the pump 26 is activated to discharge the silicone oil from the second compartment 22 by the pump 26 of the same quantity as the quantity of dissolving solution determined to be required according to the concentration detected by the concentration meter N. At this time, the same quantity of the dissolving solution as the discharged silicone oil is supplied to the first compartment 21 from the dissolving solution source (step 7-B-1). Then, the switch valve 811 is opened while the other valves 61, 311 and 321 remain closed, and the switch valves 11 and 911 are also closed to transport the dissolving solution in the first compartment 21 through the by-pass line 81 including part of circulating line 91 and part of the dialysate solution preparing line 32 to the third compartment 23 (step 7-B-2). When an increase in the internal pressure in the third compartment 23 is detected by the pressure gauge 62 (step 7-B-3), the switch valve 811 is closed and the switch valve 911 is opened to restart the circuit circulation of the solution, and then the preparation of the dialysate solution terminates (step 7-B-4).

Upon completion of the preparation of dialysate solution, the transporting pump 4 stops, the switch valve 911 is closed, and the switch valves 11, 61 are opened to supply the dissolving solution from the dissolving solution source through the dissolving solution supply line 1 to the first compartment 21 of the chamber 2. Simultaneously, the movable partitions 24, 25 are pushed by the supplied dissolving solution and move toward the third compartment 23, so that the dialysate solution in the third compartment 23 is transported through the dialysate solution transporting line 6 to the point of use (step 8).

The movement of the movable partitions 24, 25 and the transportation of the dialysate solution in the third compartment 23 to the point of use continues until the capacity of the third compartment 23 becomes zero, in other words, until dissolving solution of the same quantity as the difference between the capacity of the chamber 2 and the capacity of the second compartment 22 is filled in the first compartment 21 (step 9).

When the capacity of the third compartment 23 becomes zero, the internal pressure in the dialysate solution transporting line 6 suddenly drops. When the drop of the internal pressure in the dialysate solution transporting line 6 is detected by the pressure gauge 62, the switch valves 11, 61 are closed and the switch valves 311, 321 are opened and the transporting pump 4 is operated, and thus the dissolving solution is supplied through the dialysate solution preparing line 31 to the solution tank 5 and mixed with powder continuously supplied to the solution tank 5, and transported through the dialysate solution preparing line 32 to the third compartment 23 (step 10). The same procedures (from steps 5, 6, 7, 7-A, 8, 9 to 10, or 5, 6, 7, 7-B-1 to 7-B-4, 8, 9 to 10) are repeated to prepare the dialysate solution.

Figure 2:
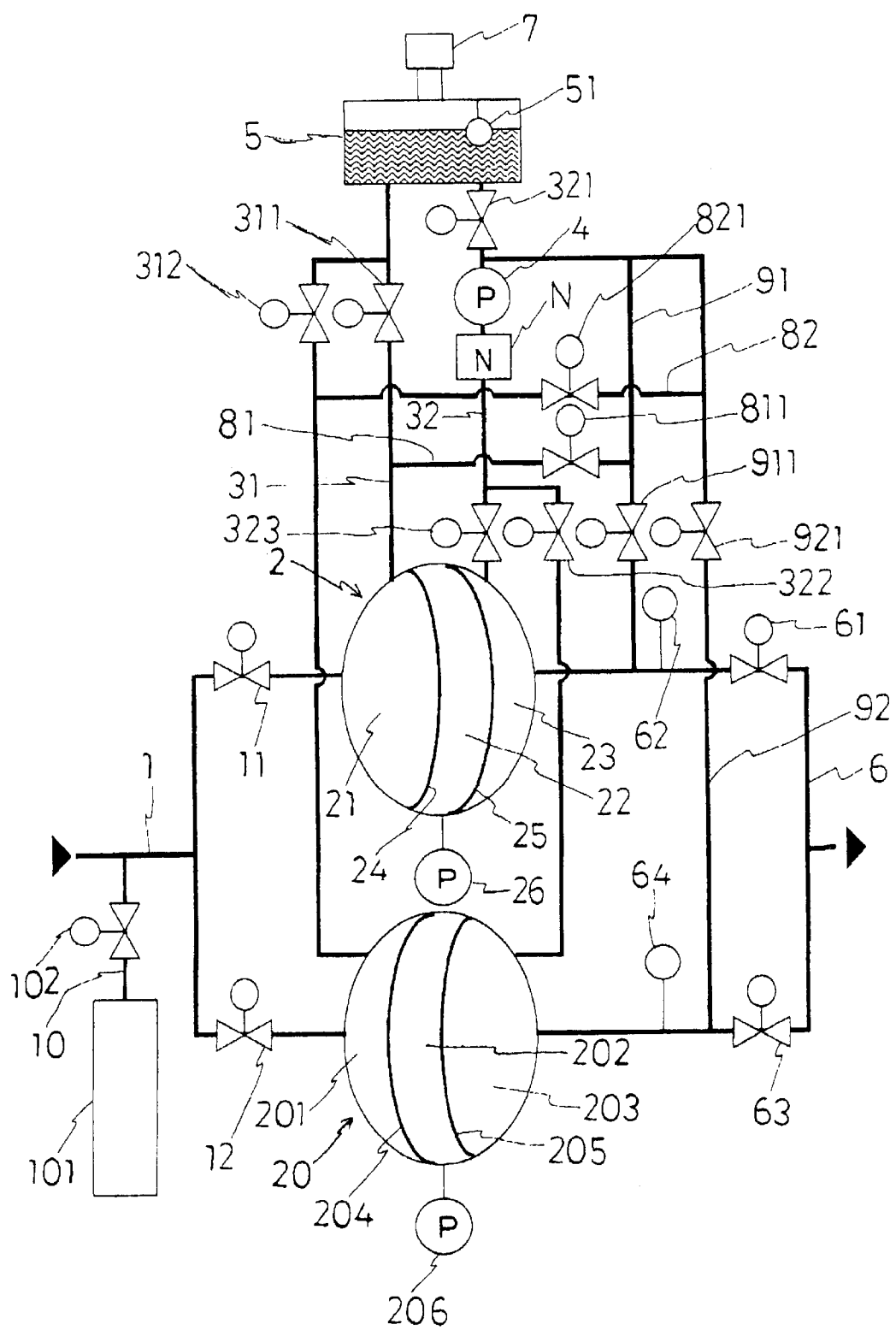
FIG. 2 is a schematic system diagram showing another embodiment of the present invention.

The apparatus for preparing dialysate solution of the present invention may be constructed in such a manner that the dissolving solution supply line 1 is provided with a second dissolving solution supply line 10 as shown in FIG. 2. The second dissolving solution supply line 10 normally comprises a second dissolving solution source 101 and a switch valve 102. The apparatus for preparing dialysate solution of the present invention may be constructed in such a manner that a second chamber 20, the inside of which is divided into three compartments 201, 202, 203 by movable partitions 204, 205, is connected to the dissolving solution supply line 1, the dialysate solution preparing lines 31, 32, and the dialysate solution transporting line 6, so that the preparation of the dialysate solution can continuously be performed as shown in FIG. 2. In the figure, reference numerals 12, 312, 322, 323, 63, 821, and 921 designate switch valves, 206 designates a pump for charging and discharging a liquid filled in the second compartment 202, 64 designates a pressure gauge, 82 designates a by-pass line, and 92 designates a circulating line.

In the case of the apparatus for preparing dialysate solution shown in FIG. 2, preparation of the dialysate solution is continuously performed by using the chamber 2 and the second chamber 20. Initially, the switch valves 11, 61 and 311 connected with the chamber 2 are opened but valves 321, 323, 811 and 911 connected to the chamber 2 are closed, and also valves 12, 63, 312, 322 and 921 connected to the chamber 20 are closed to supply the dissolving solution to the first compartment 21 of the chamber 2 as in the case of the apparatus for preparing dialysate solution shown in FIG. 1. And then the switch valves 11 and 61 are closed, the switch valves 321 and 323 are opened, and the transporting pump 4 is activated, so that the dissolving solution is supplied through the dialysate solution preparing line 31 to the solution tank 5 and mixed with powder continuously supplied to the solution tank 5, which is then transported through the dialysate solution preparing line 32 to the third compartment 23. Then, the switch valves 311 and 321 are closed and the switch valve 911 is opened to perform the circuit circulation of a solution and, if necessary, concentration adjustment is performed as in the case shown in FIG. 1, to prepare the dialysate solution.

The supply of the dissolving solution to the first compartment 201 of the second chamber 20 is performed by opening the switch valves 12, 63 while the switch valves 11, 61 are closed and the transporting pump 4 is operated and the dialysate solution is prepared. When a drop of internal pressure in the dialysate solution transporting line 6 is detected by the pressure gauge 64, the supply of the dissolving solution to the first compartment 201 of the second chamber 20 terminates and the switch valves 12, 63 are closed.

Upon completion of the preparation of the dialysate solution in the chamber 2, the transporting pump 4 is stopped, the switch valves 311, 323 and 911 are closed, and the switch valves 11 and 61 are opened to supply the dissolving solution to the first compartment 21. Simultaneously, the dialysate solution in the third compartment 23 is transported to the point of use. When a drop of the internal pressure in the dialysate solution transporting line 6 is detected by the pressure gauge 62, the supply of the dissolving solution to the first compartment 21 and the transportation of the dialysate solution to the point of use terminate, and the switch valves 11, 61 connected to the chamber 2 are closed. While the dialysate solution in the third compartment 23 is transported to the point of use, the switch valves 312, 322 connected to the chamber 20 are opened, and the transporting pump 4 is activated to start the preparation of the dialysate solution in the second chamber 20. When the transporting pump 4 is activated, the dissolving solution is supplied from the compartment 21 through the dialysate solution preparing line 31 to the solution tank 5 and mixed with powder continuously supplied to the solution tank 5, and the mixture is transported through the dialysate solution preparing line 32 to the third compartment 203 in the chamber 20. Then, the switch valves 312, 321 are closed and the switch valve 921 is opened to perform the circuit circulation of a solution, and if necessary, concentration adjustment is performed as in the case of chamber 2, to adjust the dialysate solution.

Upon completion of preparation of the dialysate solution in the second chamber 20, the transporting pump 4 is stopped, the switch valves 322 and 921 are closed, and the switch valves 12, 63 are opened to supply the dissolving solution to the first compartment 201. Simultaneously, the dialysate solution in the compartment 203 is transported to the point of use. When a drop of the internal pressure in the dialysate solution transporting line 6 is detected by the pressure gauge 64, the supply of the dissolving solution to the first compartment 201 and the transportation of the dialysate solution to the point of use terminate, and the switch valves 12, 63 are closed. While the dialysate solution in the compartment 203 is transported to the point of use, the switch valves 311, 321, 323 connected to the chamber 2 are opened, and the transporting pump 4 is activated to start the preparation of the dialysate solution with the chamber 2.

In the same manner, the supply of the dissolving solution to the chamber 2 and that to the second chamber 20, the preparation of the dialysate solution, and the transportation to the point of use are alternately repeated. The supply of the second dissolving solution can be performed by opening the switch valve 102 as appropriate.

As is clear from the description above, the liquid transporting equipment of the present invention is advantageous in terms of cost because an air filter or stirring pump is not necessary, and the number of delivering pumps can be reduced. Since a large solution tank is not necessary, miniaturization of the system itself is possible. Since there is only one delivering pump used, operating noise can significantly be reduced. Even when an abnormality in concentration is found after preparation, waste of the dialysate solution can be avoided since concentration adjustment of the dialysate solution can be performed easily.

What is claimed is:

1. An apparatus for preparing dialysate solution comprising:
   a chamber, an inside of which is divided into a first compartment, a second compartment and a third compartment by movable partitions;
   a first dissolving solution supply line for supplying a dissolving solution into the first compartment of the chamber;
   a dialysate solution preparing line connecting the first compartment and the third compartment of the chamber;
   a solution tank connected to the first compartment and a transporting pump connected to the third compartment and both of which are provided in the dialysate solution preparing line, the solution tank being connected to the transporting pump;
   powder supply means provided above the solution tank;
   a dialysate solution transporting line for transporting a dialysate solution filled in the third compartment to a point of use;
   a circulating line connecting the dialysate solution transporting line with the dialysate solution preparing line between the solution tank and the transporting pump;
   a by-pass line for bypassing the solution tank and connecting the first compartment with the third compartment via the circulating line;
   means for charging and discharging a liquid to and from the second compartment of the chamber;
   wherein the quantity of dissolving solution to be supplied to the first compartment and the quantity of dialysate solution to be transported to the third compartment can be adjusted by charging and discharging the liquid to and from the second compartment of said chamber.

2. The apparatus set forth in claim 1, wherein the circulating line is for circulating dialysate solution from the third compartment to the same compartment and comprises a line connecting an intermediate point of the dialysate solution transporting line with an intermediate point between the solution tank and the transporting pump in the dialysate solution preparing line.

3. The apparatus set forth in claim 1, wherein the by-pass line comprises a line connecting an intermediate point located between the first compartment and the solution tank in the dialysate solution preparing line with an intermediate point located between the dialysate solution transporting line and the dialysate solution preparing line in said circulating line.

4. The apparatus for preparing dialysate solution set forth in claim 1, wherein said means for charging and discharging a liquid to the second compartment is a pump.

5. The apparatus for preparing dialysate solution set forth in claim 1, wherein said liquid comprises a silicone oil.

6. The apparatus for preparing dialysate solution as set forth in claim 1, wherein a liquid level detecting sensor is provided in the solution tank.

7. The apparatus for preparing dialysate solution as set forth in claim 1, wherein a concentration meter is provided in the circuit comprising the third compartment of the chamber, the dialysate solution transporting line, the circulating line, and the dialysate solution preparing line.

8. The apparatus for preparing dialysate solution as set forth in claim 1, wherein a second dissolving solution supply line is provided in the first dissolving solution supply line.

9. The apparatus for preparing dialysate solution as set forth in claim 1, further comprising a second chamber, the inside of which is divided into first, second and third compartments by movable partitions, the first compartment of the second chamber being connected to the dissolving solution supply line, and to the dialysate solution preparing line, the third compartment of the second chamber being connected to the dialysate solution transporting line and to the dialysate solution preparing line, so that the preparation of dialysate solution can continuously be performed.

* * * * *